(12) United States Patent
Cuscuna

(10) Patent No.: US 10,485,511 B2
(45) Date of Patent: Nov. 26, 2019

(54) INTERPOSER ELECTRICAL INTERCONNECT WITH SPRING

(71) Applicant: KONINKLIJKE PHILIPS N.V., Eindhoven (NL)

(72) Inventor: Dino Francesco Cuscuna, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 33 days.

(21) Appl. No.: 15/541,770

(22) PCT Filed: Dec. 20, 2015

(86) PCT No.: PCT/IB2015/059808
§ 371 (c)(1),
(2) Date: Jul. 6, 2017

(87) PCT Pub. No.: WO2016/113617
PCT Pub. Date: Jul. 21, 2016

(65) Prior Publication Data
US 2018/0000448 A1    Jan. 4, 2018

Related U.S. Application Data

(60) Provisional application No. 62/102,785, filed on Jan. 13, 2015.

(51) Int. Cl.
*A61B 8/00* (2006.01)
*A61B 8/08* (2006.01)
*A61B 8/12* (2006.01)
*G10K 11/00* (2006.01)

(52) U.S. Cl.
CPC ............ *A61B 8/445* (2013.01); *A61B 8/0883* (2013.01); *A61B 8/12* (2013.01); *G10K 11/004* (2013.01)

(58) Field of Classification Search
CPC ......... A61B 8/445; A61B 8/0883; A61B 8/12; G10K 11/004
See application file for complete search history.

(56) References Cited

U.S. PATENT DOCUMENTS

| | | | |
|---|---|---|---|
| 5,882,310 | A | 3/1999 | Marian, Jr. |
| 2004/0044285 | A1 | 3/2004 | Flesch et al. |
| 2006/0116584 | A1 | 6/2006 | Sudol et al. |
| 2010/0249598 | A1 | 9/2010 | Smith et al. |
| 2012/0143060 | A1 | 6/2012 | Weekamp et al. |
| 2013/0002094 | A1 | 1/2013 | Toda |
| 2013/0143420 | A1 | 6/2013 | Light et al. |
| 2014/0057136 | A1 | 2/2014 | Greenman et al. |

FOREIGN PATENT DOCUMENTS

JP    2014057136 A    3/2014

*Primary Examiner* — Rex R Holmes

(57) ABSTRACT

An interposer with a spring on a surface of the interposer is disclosed. The spring may apply a force to a surface of a component adjacent to the interposer. The interposer may be secured to the surface by a fastener. The fastener may be offset from the center of the interposer. The fastener may be a fulcrum of a lever including the interposer and the spring. The spring may cause a portion of the interposer on the other side of the fastener from the spring to apply an increased amount of pressure to the surface to which the interposer is secured. A transesophageal exam ultrasound probe including an interposer is disclosed.

15 Claims, 7 Drawing Sheets

INTERPOSER ELECTRICAL INTERCONNECT WITH SPRING

This application is the U.S. National Phase application under 35 U.S.C. § 371 of International Application No. PCT/IB2015/059808, filed on Dec. 20, 2015, which claims the benefit of Provisional Application Ser. No. 62/102,785 filed Jan. 13, 2015 These applications are hereby incorporated by reference herein.

BACKGROUND

Transesophageal exam (TEE) and catheter ultrasound probes may be designed with limited external dimensions to access internal areas of the body that are inaccessible to traditional external ultrasound probes. For example, TEE probes may be positioned in the esophagus to perform echocardiography. To maintain limited external dimensions, a flexible circuit may be coupled to a transducer array and/or other hardware in the distal end of an endoscope-type device. The flexible circuit may then be coupled to a second flexible circuit that may provide power and communication with an ultrasound imaging system located at the proximal end of the device. The flexible circuits may provide a compact electrical assembly that fits within a probe designed to access internal areas of the body.

Coupling flexible circuits may be difficult and time consuming as surface soldering of individual connections may be required. The soldered connections between the flexible circuits may have poor reliability. The conductive traces within the flexible circuits may crack or break if the flexible circuit is deformed beyond a certain threshold and/or is deformed repeatedly. These deficiencies in coupling flexible circuits may lead to poor reliability of TEE and catheter ultrasound probes in a clinical setting. It may also increase the expense and difficulty of repairing malfunctioning probes. For example, it may not be feasible to de-solder the flexible circuits, so if one circuit is malfunctioning, both flexible circuits and associated components may need to be replaced.

SUMMARY

An example apparatus according to an embodiment of the disclosure may include an interposer having a first surface and a second surface opposite the first surface, and the interposer further having an opening that extends through the first surface and through the second surface, wherein the opening may be configured to accept a fastener, and a spring coupled to the first surface of the interposer, wherein the spring may be configured to apply a force between a component surface and the first surface when the component surface is adjacent to the first surface. The opening may be offset from a center of the interposer. The interposer may further include a pad field on the first surface, wherein the pad field and the spring may be on opposing sides of the opening in the first surface.

An example ultrasound probe according to an embodiment of the disclosure may include a backing layer having a lower surface, a flexible circuit covering a portion of the lower surface of the backing layer, an interposer having a surface and the interposer adjacent to the flexible circuit opposite the lower surface of the backing layer, a fastener that may be configured to secure the interposer and flexible circuit against the lower surface of the backing layer, and a spring disposed at a first end of the interposer and disposed between the surface of the interposer and the backing layer, the spring may be configured to provide a force to bias a first end of the interposer away from the backing layer and to bias a second end of the interposer toward the backing layer, and a printed circuit board adjacent to the interposer opposite the flexible circuit.

An example method according to an embodiment of the disclosure may include applying a force to a first portion of a surface of a component with a spring adjacent to a first end of an interposer that is adjacent to the component; and distributing, with a fulcrum, the force to a second end of the interposer to apply a force to a second portion of the surface of the component, wherein the second end and first end of the interposer are on opposite sides of the fulcrum.

An example method according to an embodiment of the disclosure may include introducing a transesophageal ultrasound probe into a patient's mouth or nasal cavity, wherein the transesophageal ultrasound probe includes: a backing layer having a lower surface, a flexible circuit covering a portion of the lower surface of the backing layer, an interposer having a surface and the interposer adjacent to the flexible circuit opposite the lower surface of the backing layer, a fastener that may be configured to secure the interposer and flexible circuit against the lower surface of the backing layer, and a spring disposed at a first end of the interposer and disposed between the surface of the interposer and the backing layer, the spring may be configured to provide a force to bias a first end of the interposer away from the backing layer and to bias a second end of the interposer toward the backing layer, and a printed circuit board adjacent to the interposer opposite the flexible circuit; guiding the transesophageal ultrasound probe through the patient's laryngopharynx; guiding the transesophageal ultrasound probe into the patient's esophagus; positioning the transesophageal ultrasound probe in a desired location in the patient's gastrointestinal track; and acquiring an ultrasound image.

DETAILED DESCRIPTION

Figure 1:
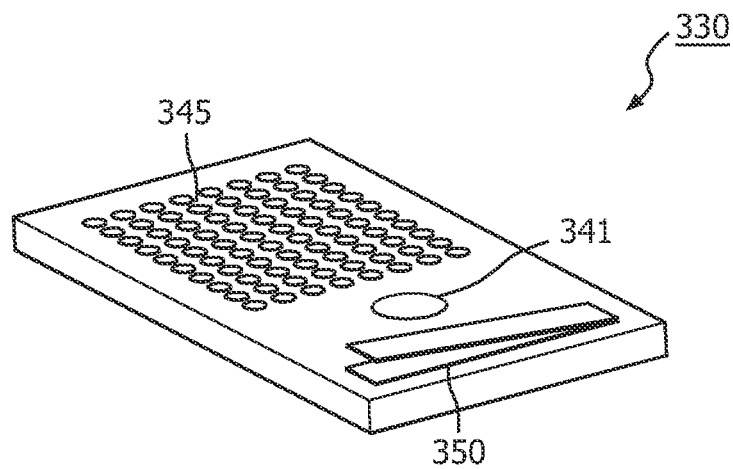
FIG. 1 is a schematic illustration of an interposer according to an embodiment of the disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

In many traditional external probes, a flexible circuit is coupled to a transducer array. The flexible circuit may be able to bend, fold and/or twist. This may allow the flexible circuit to curve around another component and/or conform to a surface. The degree of flexibility of the flexible circuit may be determined, at least in part, by materials chosen for the flexible circuit (e.g. films, conductive elements, circuit components). The flexible circuit may include an insulating polymer film with conductive elements (e.g., wires) applied on one surface. A second insulating polymer film may be applied over the conductive elements and first polymer film. The conductive elements may be made of metals, conductive polymers, or other conductive materials. Some flexible circuits may include multiple alternating layers of elements and insulating film. The flexible circuit is then coupled to an interposer electrical interconnect, which electrically couples the flexible circuit to a printed circuit board. The printed circuit board (PCB) may provide power and control signals to the transducer array through the interposer and flexible circuit. The PCB may also receive signals from the transducer array through the interposer and flexible circuit. The interposer may eliminate the need to solder electrical connections directly between the flexible circuit and the PCB. The interposer may provide more reliable electrical coupling and easier disassembly. Individual components may be upgraded and/or replaced when faulty rather than replacing an entire flexible circuit/PCB assembly. The interposer may provide for ultrasound probes with greater reliability and easier repair of ultrasound probes that require maintenance.

An interposer may be secured to provide a uniform pressure distribution across all of the electrical interconnects included on the interposer to maintain electrical coupling between the flexible circuit and the PCB. Many traditional external ultrasound probes couple the interposer to the probe with two or more screws. However, the use of screws in some TEE and catheter probes may not be feasible due to the limited internal space. For example, the space requirements of the screws may prevent some desired electrical connections from being placed in a probe. The screws may also interrupt the heat flow path of the probe, reducing the thermal efficiency of the probe. In some probes, the dimensions of the probe may be small enough that the screws are within the acoustical path of a transducer stack in the probe and may introduce artifacts in the image acquired by the probe. The presence of artifacts may not be acceptable in some imaging applications.

For ultrasound probes with limited external dimensions (e.g. TEE and catheter), an alternative configuration for securing an interposer may be desirable to maintain adequate area on components for electrical connections and/or reduce image artifacts.

An interposer secured with a single fastener offset from a transducer stack to avoid the acoustical path may provide adequate space for electrical connections, traces, and/or other elements in other components such as a PCB and/or flexible circuit. However, in some interposer designs, the offset fastener may not provide a uniform distribution of pressure over a field pad of the interposer. This may lead to inadequate coupling between circuits located at areas of the interposer where less pressure is applied.

FIG. 1 is a schematic illustration of an interposer 330 according to an embodiment of the disclosure. The interposer 330 may include a pad field 345 that may include electrical interconnects for electrically coupling two or more electrical components. For example, the interposer 330 may be disposed between a flexible circuit and a PCB to electrically couple various electrical components. The interposer 330 may include an opening 341 configured to accept a fastener for securing the interposer 330. In some embodiments, the opening 341 may be offset from the center of the interposer 330. As shown in FIG. 1, the opening 341 may be outside of the pad field 345, however, in some embodiments, the pad field 345 may extend to and/or beyond the opening 341. For example, the opening 341 may be surrounded by the pad field 345 in some embodiments. The interposer 330 may further include a spring 350 at an end of the interposer 330. Although spring 350 is illustrated as a cantilever spring in FIG. 1, other types of springs may be used.

The spring 350 may be configured to apply a force to a surface (not shown) to which the interposer 330 is adjacent when the interposer 330 is secured by a fastener (not shown) that passes through opening 341. The fastener may act as a fulcrum to a lever that includes the spring 350 on the interposer 330. The force applied by the spring 350 to the surface may increase the pressure applied to an end of the interposer 330 opposite the spring. As a result, the spring 350 may improve the uniformity of pressure applied to the interposer 330 and/or the pad field 345, which may improve the electrical connections of the pad field 345.

Figure 2:
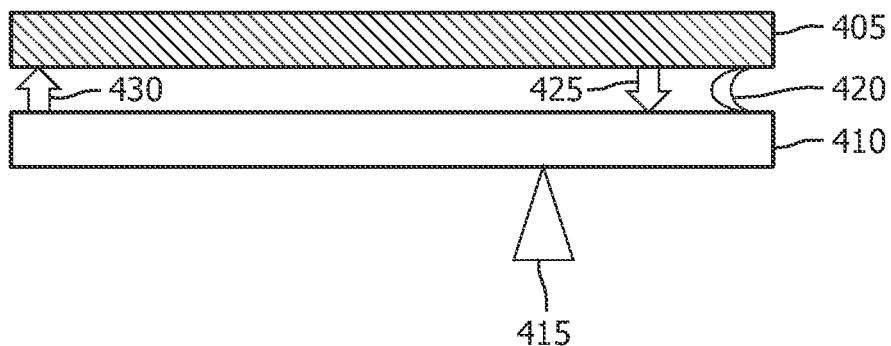
FIG. 2 is a simplified schematic illustration of an interposer according to an embodiment of the disclosure.

FIG. 2 is a simplified schematic diagram illustrating the forces applied to an interposer according to an embodiment of the disclosure. An interposer 410 may be secured against a component 405 by a fastener. The component 405 may be, for example, a flexible circuit, a PCB, and/or other electrical component. Although not shown in FIG. 2, the fastener may pass through both the interposer 410 and at least partially through component 405. A fulcrum 415 is illustrated in FIG. 2, which represents the fastener used to secure the interposer 410. The interposer 410 may act as lever coupled to the fulcrum 415. The interposer 410 may include a spring 420 on a surface of the interposer 410, which is adjacent to a lower surface of component 405. The spring 420 may provide a force between the lower surface of component 405 and the upper surface of the interposer 410 to cause the portion of the interposer 410 from the fulcrum 415 to the end near the spring 420 to be biased away from the lower surface of the component 405, as indicated by arrow 425. The lever action between the interposer 410 and fulcrum 415 may cause the force applied by the spring 420 to increase the pressure of the interposer 410 against a portion of the lower surface of component 405 on the opposite side of the fulcrum 415 from the spring 420, as indicated by arrow 430. A portion of the interposer 410 may be biased away from the component 405 on the side of the fulcrum 415 with the spring 420, and a portion of the interposer 410 on the opposite side of the fulcrum 415 from the spring 420 may be biased towards the component 405. The lever including the fulcrum 415 and interposer 410 may increase the uniformity of the distribution of pressure applied across the interposer 410 when the spring 420 is used to apply a force to one side of the lever. The fulcrum 415 may distribute the force applied by the spring 420 on one end of the interposer 410 to another end of the interposer 410.

Figure 3A:
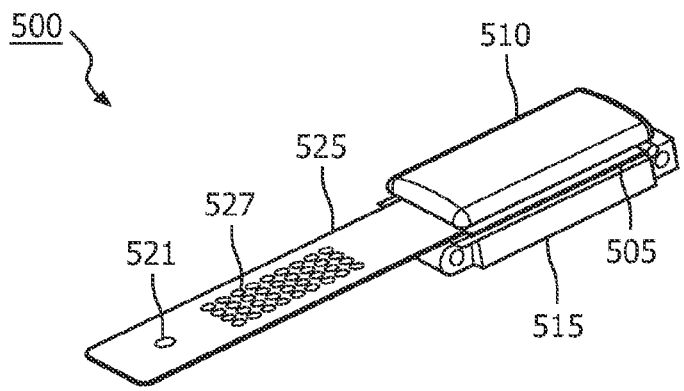
FIG. 3A is a schematic illustration of an ultrasound transducer and flexible circuit according to an embodiment of the disclosure.
Figure 3B:
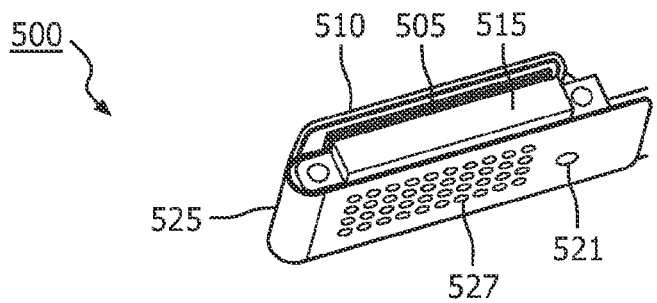
FIG. 3B is a schematic illustration of the flexible circuit wrapped under the ultrasound transducer illustrated in FIG. 3A according to an embodiment of the disclosure

FIGS. 3A-B, 4, 5A-B, and 6 are schematic illustrations of assembly of an ultrasound probe 500 according to an embodiment of the disclosure. Reference to the "top" and "bottom" orientation of the probe 500 in FIGS. 3A-B, 4, 5A-B, and 6 is made to facilitate the description of the probe 500, and is not intended to limit embodiments of the disclosure to specific spatial orientations and/or configurations of the ultrasound probe 300. FIG. 3A is an isometric view of the top of probe 500. A transducer stack 505 with a window 510 on top may be coupled to a backing layer 315. A flexible circuit 525 may be coupled to the transducer stack 505. The flexible circuit may include conductors 527 and an opening 526 configured to accept a fastener (not shown). FIG. 3B is an isometric view of the bottom of the probe 500. The flexible circuit 525 may be wrapped under the backing layer 515. The backing layer 515 may include an opening (not shown) that aligns with opening 526 configured to accept a fastener.

Figure 4:
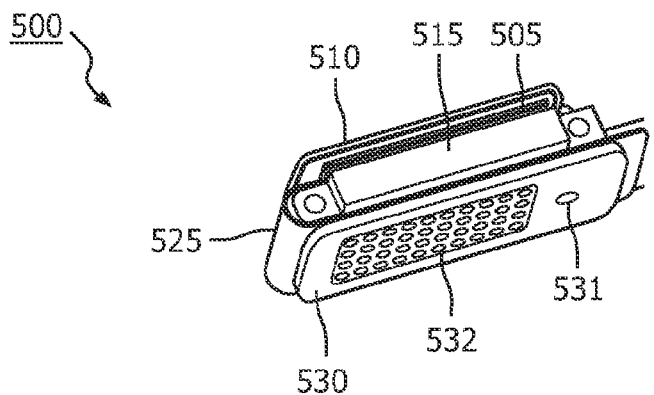
FIG. 4 is a schematic illustration of an interposer coupled to the ultrasound transducer and flexible circuit illustrated in FIGS. 3A-B according to an embodiment of the disclosure.

FIG. 4 is an isometric view of the bottom of the probe 500 with an interposer 530 positioned against the flexible circuit 525. The interposer 530 may be implemented using interposer 330 illustrated in FIG. 1. The interposer 530 includes a pad field 532 on both of its surfaces. The pad field 532 on one surface of the interposer 530 may be electrically coupled to the pad field 532 on the other surface of the interposer 530. The pad field 532 may be electrically coupled to one or more of the conductors 527 of the flexible circuit 525 when positioned against the flexible circuit 525. The interposer 525 may include a spring on the surface positioned against the flexible circuit 525. Although not visible in FIG. 4, the spring may be similar to spring 350 illustrated in FIG. 1. The interposer 530 may include an opening 531 which may align with opening 526 in the flexible circuit 525. The opening 531 may be configured to accept a fastener (not shown).

Figure 5A:
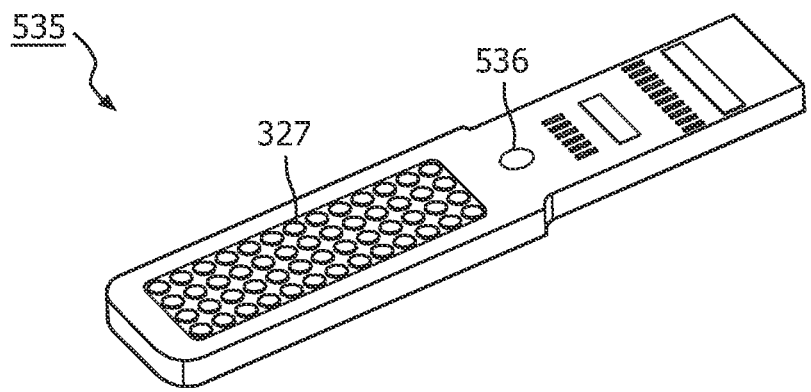
FIG. 5A is a schematic illustration of a printed circuit board according to an embodiment of the disclosure.
Figure 5B:
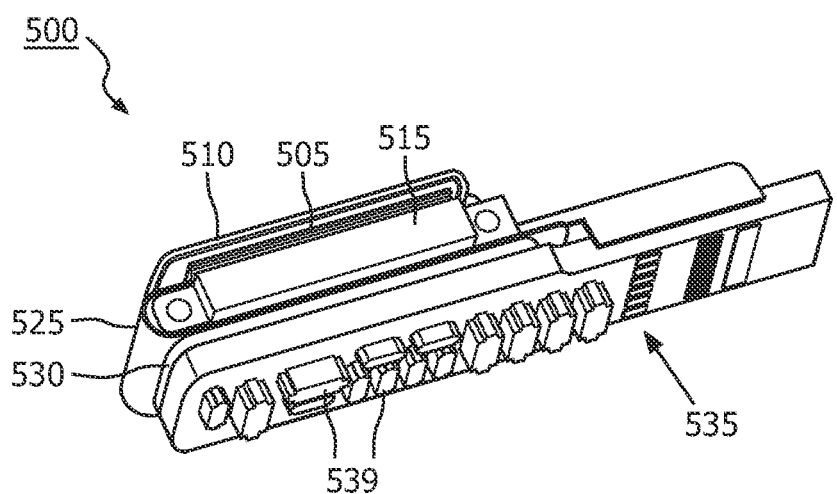
FIG. 5B is a schematic illustration of the printed circuit board illustrated in FIG. 5A coupled to the interposer illustrated in FIG. 4.

FIG. 5A is an isometric view of the top of a printed circuit board (PCB) 535. The PCB 535 may include conductors 537 and opening 536 configured to accept a fastener. FIG. 5B is an isometric view of the bottom of the probe 500 with the PCB 535 positioned against the interposer 530. The PCB 535 may include circuits 539. The circuits 539 may be electrically coupled to the conductors 537. One or more of the conductors 537 may be electrically coupled to pad field 532 of the interposer 530 when the PCB 535 is positioned against the interposer 530. The interposer 530 may electrically couple the PCB 535 to the flexible circuit 525. Although not visible in FIG. 5B, opening 536 may align with opening 526 in the flexible circuit 525 and opening 531 in the interposer 530.

Figure 6:
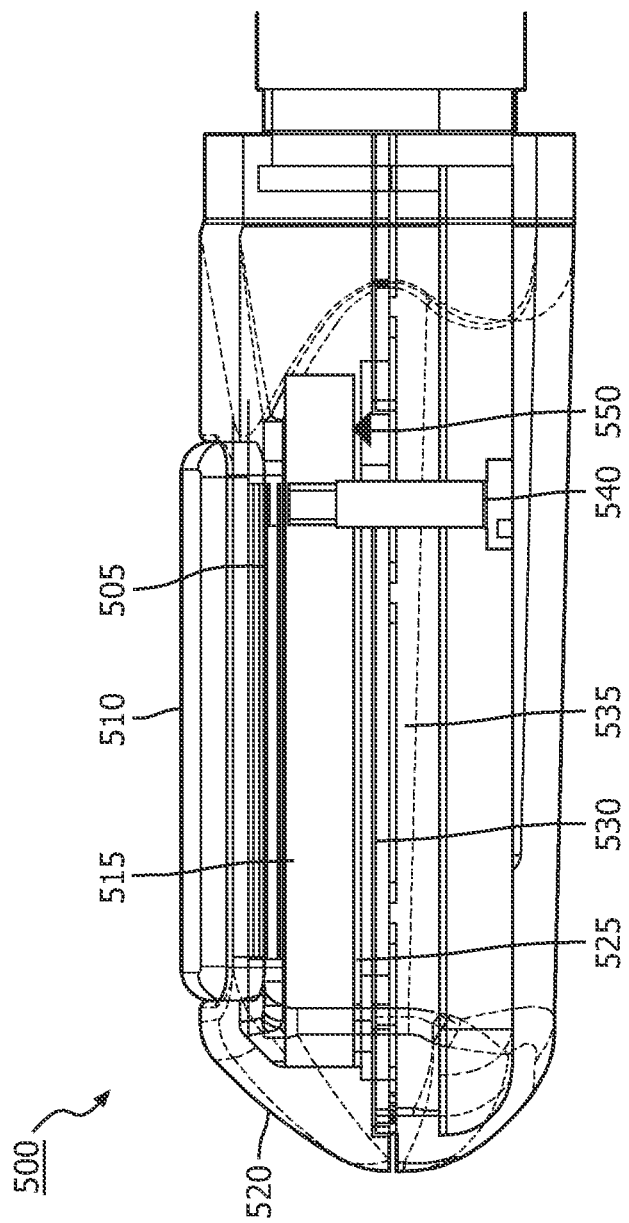
FIG. 6 is a schematic illustration of a TEE probe according to an embodiment of the disclosure.

FIG. 6 is a schematic illustration of the ultrasound probe 500 including an interposer according to an embodiment of the disclosure. The probe 500 may include a transducer stack 505 with a window 510 on top. The transducer stack 505 may be coupled to a backing layer 515. A flexible circuit 525 may be coupled to the transducer stack 505 and wrapped around the backing layer 515 such that the flexible circuit 525 covers at least a portion of a bottom surface of the backing layer 515. An interposer 530 may be placed against a surface of the flexible circuit 525 opposite the backing layer 515. A PCB 535 may be placed against a surface of the interposer 530 opposite the flexible circuit 525. A fastener 540 may pass through openings 536, 531, 526 in the PCB 535, interposer 530, flexible circuit 525, and an opening in the backing layer 515 to secure the electrical components to the backing layer 515. The interposer 530 may include a spring 550 on a surface adjacent to the flexible circuit 525. The spring 550 may improve the distribution of pressure applied by the fastener 540 such that a pad field (not shown) of the interposer 530 applies a more uniform pressure to the flexible circuit 525 and/or PCB 535. The probe 500 may be enclosed by a protective shell 520. The protective shell 520 may be a metal, polymer, or other suitable material. In some embodiments, the protective shell 520 may protect the internal components of the probe 500 from moisture, electrical interference, dust, and/or biological contamination.

In some embodiments, the fastener 540 is offset from the lengthwise (e.g., longitudinal) center of the interposer 530. As shown in FIG. 3, the fastener 540 is also offset from the lengthwise (e.g., longitudinal) center of the transducer stack 505. This may reduce or eliminate artifacts generated by the fastener 540 in images acquired by the probe 500. The offset position of the fastener 540 may minimize disruption of thermal dissipation from the transducer stack 505. The fastener 540 may be a screw, a solid pin, or a coil spring pin. Other fastener types may also be used.

In some embodiments, the spring 550 is a stainless steel cantilever spring. In some embodiments, the spring 550 is a coil spring. Other spring types and materials may also be used. The spring 550 may be soldered and/or glued to the interposer 530. In some embodiments, the spring 550 may not be secured to the interposer 530 and may be held in place by friction and/or compression. In some embodiments, the interposer 530 may include an indentation in a surface configured to retain the spring 550. In some embodiments, the interposer 530 may be manufactured to include the spring 550 as an integrated portion of the interposer 530. That is, the spring 550 may be formed in a surface of the interposer 530 of the material used to form the surface of the interposer 530. In some embodiments, the spring 550 is offset from the lengthwise (e.g., longitudinal) center of the interposer 530. The spring 550 may be located at an end of the interposer 530 opposite a pad field (not shown). In some embodiments, the fastener 540 may be located between the pad field and the spring 550.

In some embodiments, the spring 550 may be in contact with and/or coupled to a lower surface of the backing layer 515. The spring 550 may apply a force between the backing layer 515 and the interposer 530 on one side of the fastener 540. The spring may be positioned at a first end of the interposer 530 and disposed between the surface of the interposer and the backing layer. The spring 550 may provide a force to bias a first end of the interposer away from the backing layer 515 and to bias a second end of the interposer 530 toward the backing layer 515. The two ends may be on opposite sides of the fastener 540. In some embodiments, the spring 550 may contact the interposer 530 and the backing layer 515. In some embodiments, the spring 550 may apply the force through the flexible circuit 525.

Embodiments of the probes of the present disclosure may be used as a TEE ultrasound probe. A TEE ultrasound probe is often implemented at the distal end of a flexible endoscope-type device. The TEE ultrasound probe may be guided through tortuous cavities within the body for placement for imaging. For example, a TEE probe may be inserted down the esophagus from which the ultrasound transducer may scan the heart for diagnostic imaging and/or monitoring of a medical procedure (e.g., stent placement). Unlike external ultrasound probes, the TEE probe may not have to contend with the chest wall, ribs, or lungs obscuring a view of the heart. The TEE ultrasound probe implemented using an interposer, such as the probes illustrated in FIG. 3, may be less expensive to manufacture and/or more reliable in a clinical environment. The use of an interposer may reduce the number of required soldered connections, which may reduce the number of solder failures between circuits, electrical connections, and/or components. The interposer including a spring may provide reliable compression to maintain electrical connections through the interposer during navigation of the TEE probe. The interposer may allow a PCB to be included in the TEE probe rather than an additional flexible circuit. A PCB may be more robust than a second flexible circuit, reducing the risk of cracking during probe navigation. The PCB may be capable of providing a larger number and/or variety of electrical circuits than a flexible circuit.

When a TEE ultrasound probe implemented using an interposer according to an embodiment of the disclosure is repaired, disassembly may be faster and less costly than a traditional TEE probe having two flexible circuits. No de-soldering of components may be required in some embodiments. The offset fastener may be removed and the remaining components may then be separated. Once separated, individual components may be repaired, retained, or replaced. The TEE probe may then be reassembled as described in reference to FIG. 3 and returned for use in the clinic.

Although embodiments of the present disclosure have been described with reference to a TEE ultrasound probe, it is also envisioned that the embodiments of the present disclosure can be extended to other ultrasound probes configured for imaging, for example, where limited probe external dimensions may be desired, such as catheter ultrasound probes. Accordingly, the embodiments of the present disclosure may be used to obtain and/or record image information related to, but not limited to renal, testicular, breast, ovarian, uterine, thyroid, hepatic, lung, musculoskeletal, splenic, cardiac, arterial and vascular systems.

Further, the present systems, apparatuses, and methods, may also be extended to any small parts imaging where an interposer may be desired. Suitable ultrasonic imaging systems may include a Philips® ultrasound system which may, for example, support a conventional broadband linear array transducer, two dimensional array, and/or three dimensional array transducer that may be suitable for small-parts imaging.

Figure 7:
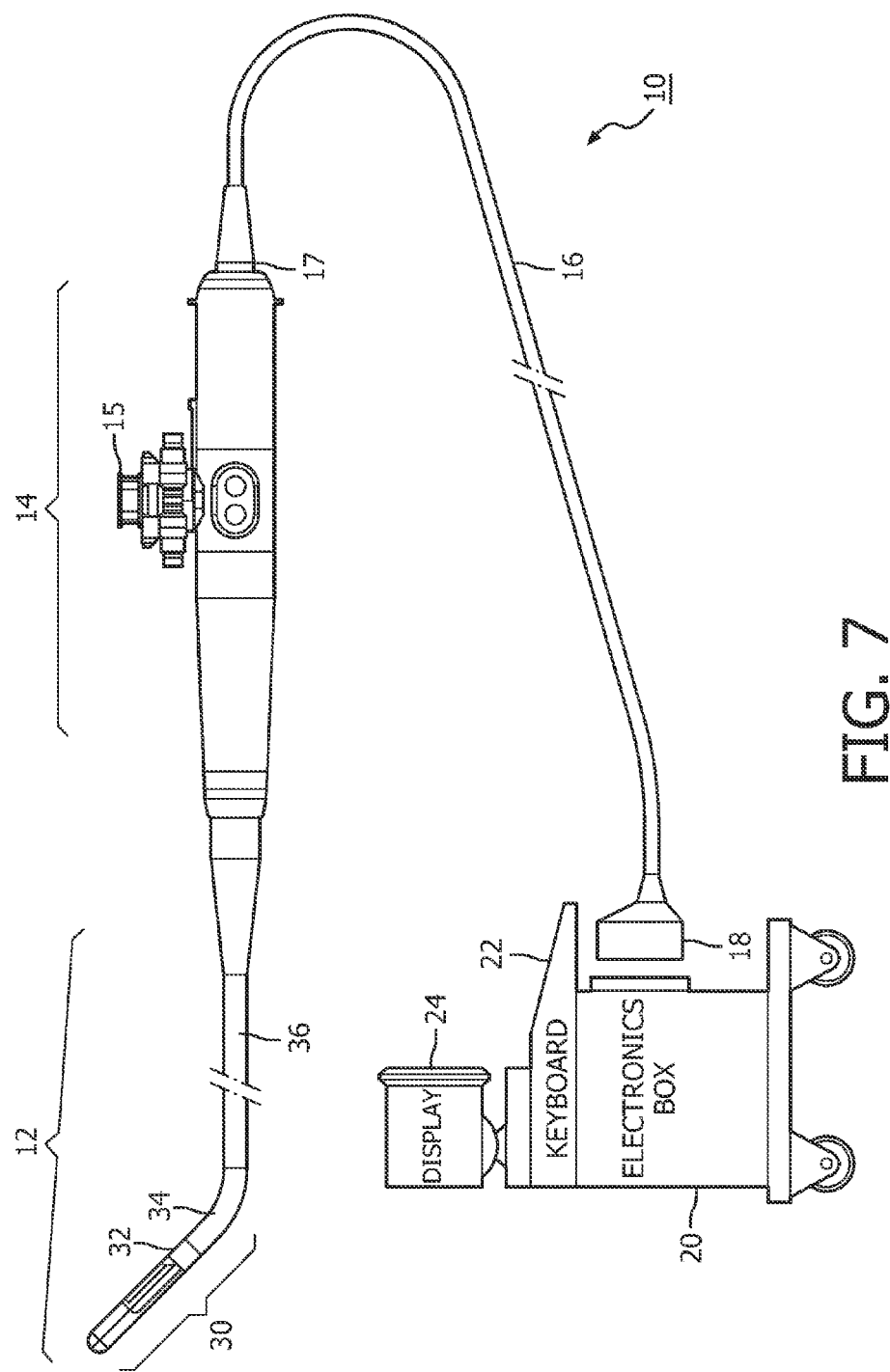
FIG. 7 is a schematic illustration of an ultrasound imaging system according to an embodiment of the disclosure.

An example ultrasound system that may include an ultrasound probe according to an embodiment of the disclosure is illustrated in FIG. 7. The imaging system 10 may be a transesophageal exam (TEE) system. The imaging system 10 may include a TEE probe 12 with a probe handle 14 connected by a cable 16, a strain relief 17, and a connector 18 to an electronics box 20. In some embodiments, TEE probe 12 may be implemented using ultrasound probe 500 illustrated in FIG. 6. The electronics box 20 may interface with a keyboard 22 and provide imaging signals to a video display 24. The electronics box 20 may include a transmit beam former, a receive beam former, and an image generator. The electronics box 20 may further include a volume renderer for three dimensional images, a graphics processor for additional display elements on the video display 24, and/or a B-mode processor for Doppler imaging. The TEE probe 12 may have a distal part 30 connected to an elongated flexible or semi-flexible body 36. The proximal end of elongated part 36 may be connected to the distal end of probe handle 14. Distal part 30 of probe 12 may include a rigid region 32 and a flexible region 34, which may be connected to the distal end of elongated body 36. The probe handle 14 may include a positioning control 15 for articulating flexible region 34 and thus orienting rigid region 32 relative to tissue of interest. The elongated semi-flexible body 36 may be constructed and arranged for insertion into the esophagus.

Figure 8:
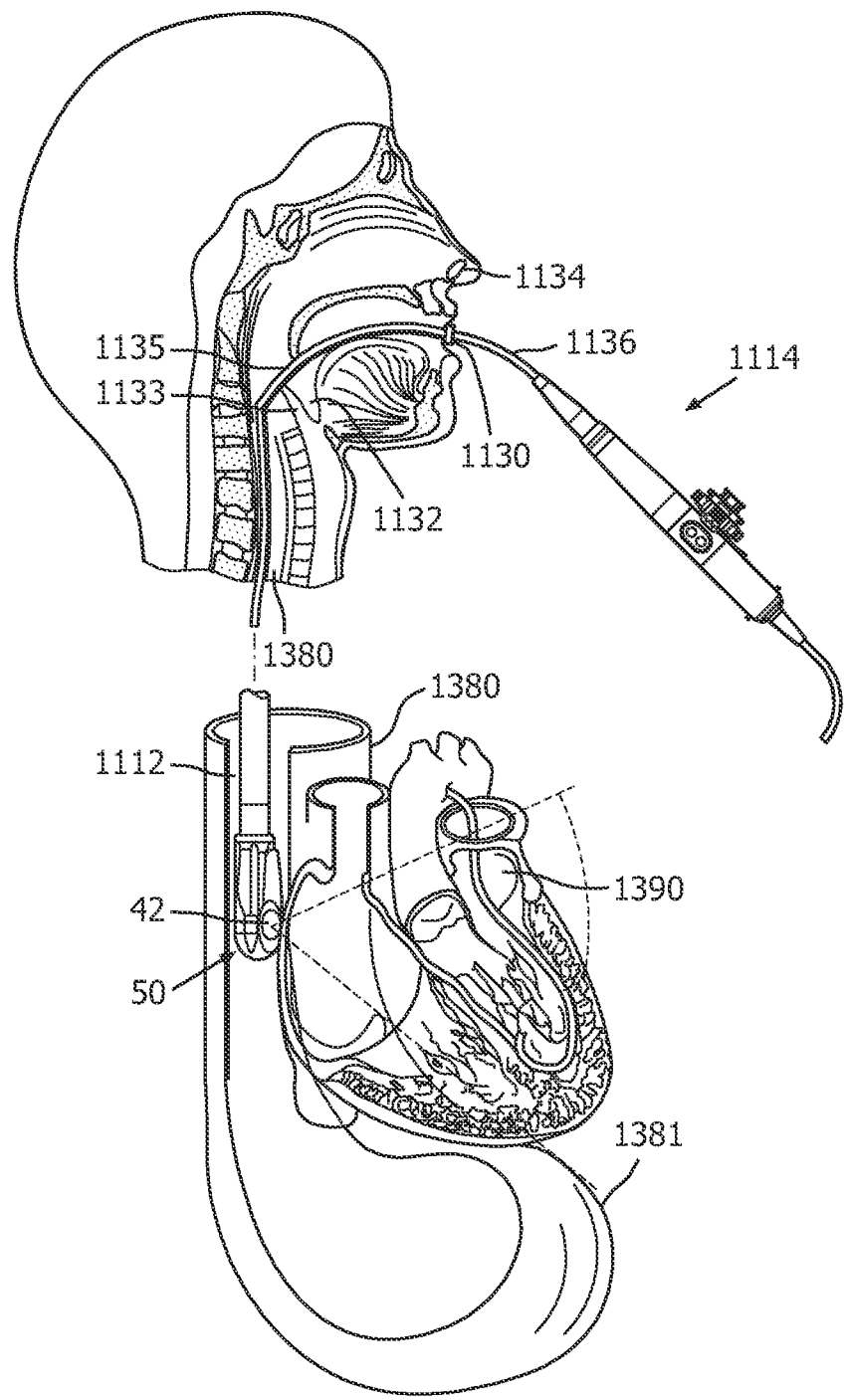
FIG. 8 is a schematic illustration of an ultrasound probe according to an embodiment of the disclosure.

FIG. 8 is a schematic illustration of a TEE probe 1112 used according to an embodiment of the disclosure. The TEE probe 1112 may be implemented using TEE probe 12 and imaging system 10 illustrated in FIG. 7. A clinician may introduce the TEE probe 1112 with an introducer 1135 through the mouth 1130, laryngopharynx 132 into the esophagus 1380. After moving the probe and the introducer past uvula 1133, distal part 50 of the probe 1112 is positioned inside the gastrointestinal (GI) track at a desired location. Alternatively, a clinician introduces the probe 1112 through the nasal cavity 1134 to the esophagus 1380. Distal part 50 with transducer array 42 may be positioned inside the esophagus 1380 as shown or the fundus of the stomach 1381. To image the heart 1390, the transmit beamformer focuses the emitted pulses at desired depths, and the receive beamformer detects echoes from structures in the thoracic cavity.

Figure 9:
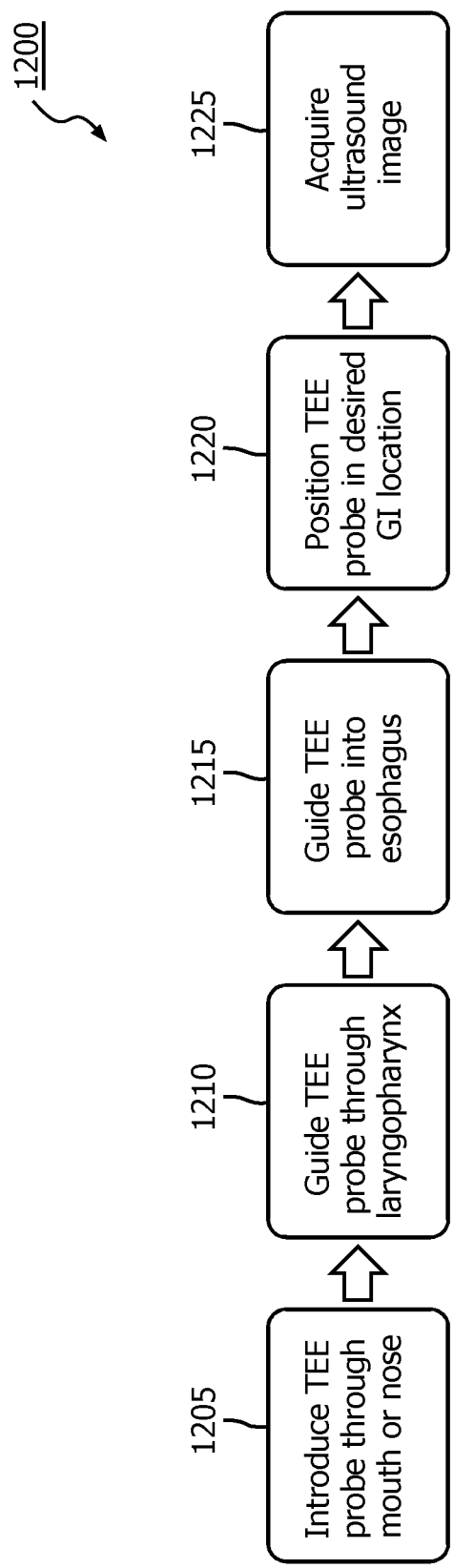
FIG. 9 is a flow chart of a method according to an embodiment of the disclosure.

FIG. 9 is a flow chart of a method 1200 of using a TEE probe according to an embodiment of the invention. In some embodiments, the method may be performed using the TEE probe 1112 illustrated in FIG. 8 or TEE probe 12 and imaging system 10 illustrated in FIG. 7. In Step 1205, the TEE probe may be introduced into a patient through the mouth or nose. The clinician may then guide the TEE probe through the laryngopharynx at Step 1210. The TEE probe may then be guided into the esophagus of the patient at Step 1215. Once in the esophagus, the TEE probe may be positioned to a desired location within the GI track (e.g., portion of esophagus, stomach) at Step 1220. The clinician may then use the TEE probe to acquire an ultrasound image at Step 1225. The image may be of the heart, another organ, and/or a medical device. In some embodiments, ultrasound images may be acquired during Steps 1205-1220. Acquiring images during movement of the TEE probe may assist with guidance and/or positioning of the probe.

Certain additional advantages and features of this invention may be apparent to those skilled in the art upon studying the disclosure, or may be experienced by persons employing the novel system and method of the present invention, chief of which is that a more reliable TEE and catheter ultrasound devices and methods of operation thereof are provided. Another advantage of the present systems and method is that conventional medical image systems can be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the previous discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound probe, comprising:
   a backing layer having a lower surface;
   a flexible circuit covering a portion of the lower surface of the backing layer;
   an interposer including:
      a first surface and a second surface opposite the first surface, the first surface adjacent to the flexible circuit opposite the lower surface of the backing layer;
      a pad field on the first surface at a first end of the interposer; and
      an opening between the first end and a second end of the interposer, the opening extending through the first surface and through the second surface;
   a fastener that passes through the opening in the interposer, the fastener configured to secure the interposer and flexible circuit against the lower surface of the backing layer; and
   a spring disposed at the second end of the interposer and disposed between the first surface of the interposer and the backing layer, the spring configured to provide a force to bias the second end of the interposer away from the backing layer and to bias the first end of the interposer toward the backing layer; and
   a printed circuit board adjacent to the second surface of the interposer opposite the flexible circuit.

2. The ultrasound probe of claim 1, wherein the opening is offset from a center of the interposer.

3. The ultrasound probe of claim 1, wherein the pad field and the spring are on opposing sides of the opening in the first surface.

4. The ultrasound probe of claim 1, wherein the spring is a cantilever spring.

5. The ultrasound probe of claim 1, wherein the spring is a coil spring.

6. The ultrasound probe of claim 1, wherein the spring is offset from a center of the interposer.

7. The ultrasound probe of claim 1, wherein the spring is soldered to the first surface of the interposer.

8. The ultrasound probe of claim 1, wherein the spring is an integrated component of the first surface of the interposer.

9. The ultrasound probe of claim 1, wherein the spring is stainless steel.

10. The ultrasound probe of claim 1, further comprising a transducer stack coupled to an upper surface of the backing layer, wherein the flexible circuit is coupled to the transducer stack and wrapped around to the lower surface of the backing layer.

11. The ultrasound probe of claim 10, further comprising a protective shell surrounding the fastener, printed circuit board, interposer, flexible circuit, backing layer, and a portion of the transducer stack.

12. The ultrasound probe of claim 10, wherein the fastener is offset from a longitudinal center of the transducer stack.

13. The ultrasound probe of claim 1, wherein the fastener is a screw.

14. The ultrasound probe of claim 1, wherein the fastener is a pin.

15. The ultrasound probe of claim 1, wherein the flexible circuit and printed circuit board include openings configured to accept the fastener, wherein the openings are aligned to each other.

* * * * *